United States Patent
Fujiya et al.

(10) Patent No.: US 10,576,126 B2
(45) Date of Patent: Mar. 3, 2020

(54) ANTITUMOR AGENT

(71) Applicant: NATIONAL UNIVERSITY CORPORATION ASAHIKAWA MEDICAL UNIVERSITY, Asahikawa-shi (JP)

(72) Inventors: Mikihiro Fujiya, Asahikawa (JP); Hiroaki Konishi, Asahikawa (JP); Kentaro Moriichi, Asahikawa (JP)

(73) Assignee: National University Corporation Asahikawa Medical University, Asahihawa-shi, Hokkaido (JP)

( * ) Notice: Subject to any disclaimer, the term of this patent is extended or adjusted under 35 U.S.C. 154(b) by 0 days.

(21) Appl. No.: 16/071,610

(22) PCT Filed: Jan. 19, 2017

(86) PCT No.: PCT/JP2017/001803
§ 371 (c)(1),
(2) Date: Jul. 20, 2018

(87) PCT Pub. No.: WO2017/126626
PCT Pub. Date: Jul. 27, 2017

(65) Prior Publication Data
US 2019/0022172 A1    Jan. 24, 2019

(30) Foreign Application Priority Data

Jan. 20, 2016  (JP) ................. 2016-009224

(51) Int. Cl.
| | | |
|---|---|---|
| A61K 38/12 | (2006.01) | |
| A61K 38/00 | (2006.01) | |
| A61K 33/26 | (2006.01) | |
| A61P 1/00 | (2006.01) | |
| A61P 35/00 | (2006.01) | |

(52) U.S. Cl.
CPC .............. *A61K 38/12* (2013.01); *A61K 33/26* (2013.01); *A61K 38/00* (2013.01); *A61P 1/00* (2018.01); *A61P 35/00* (2018.01)

(58) Field of Classification Search
CPC ...... A61K 36/02; A61K 36/03; A61K 36/185; A61K 33/26; A61K 38/00; A61K 38/12; A61P 1/00; A61P 35/00
See application file for complete search history.

(56) References Cited

U.S. PATENT DOCUMENTS

| | | | |
|---|---|---|---|
| 4,767,611 A | 8/1988 | Gordon | |
| 2012/0135002 A1 | 5/2012 | Moura et al. | |
| 2013/0157932 A1* | 6/2013 | Barasch ................. | A61K 38/17 514/2.8 |

FOREIGN PATENT DOCUMENTS

| | | |
|---|---|---|
| JP | 2009-028030 A | 2/2009 |
| JP | 2012-532925 A | 12/2012 |
| WO | 2006078717 A2 | 7/2006 |

OTHER PUBLICATIONS

Extended European Search Report for European Application No. 17741503.1, dated Dec. 21, 2018, 7 pages.
Cousin et al., PLoS One, 7(3):1-12 (2012).
Frederick et al., Biochemistry, 20(9):2432-36 (1981).
Goldin et al., Nutr Cancer, 25(2):197-204 (1996).
International Search Report for International Application No. PCT/JP2017/001803, dated Feb. 21, 2017.
Jan et al., Cell Death and Differentiation, 9:179-88 (2002).
Konishi et al., Nature Communications, 7(12365):1-12 (2016).
Manning et al., Current Medicinal Chemistry, 16:2416-29 (2009).
Marchesi et al., PLoS One, 6(5):1-8 (2011).
Sobhani et al., PLoS One, 6(1):1-7 (2011).

* cited by examiner

*Primary Examiner* — Marcela M Cordero Garcia
(74) *Attorney, Agent, or Firm* — RatnerPrestia

(57) ABSTRACT

[Problem] To provide a highly safe and efficacious antitumor agent that is derived from probiotics.
[Solution] The present invention relates to an antitumor agent comprising a compound represented by formula (1) or a complex thereof as an active ingredient. In formula (1): $R^1$ represents a hydrogen atom or a hydroxymethyl group; $R^2$ represents a hydrogen atom, a methyl group or a hydroxymethyl group; and $R^3$, $R^4$ and $R^5$ each independently represent a methyl group, an $N^5$-(trans-5-hydroxy-3-methylpent-2-enoyl) group, an $N^5$-(cis-5-hydroxy-3-methylpent-2-enoyl) group or an $N^5$-(trans-4-carboxy-3-methylpent-2-enoyl) group. According to the present invention, a highly safe and efficacious antitumor agent can be provided.

(1)

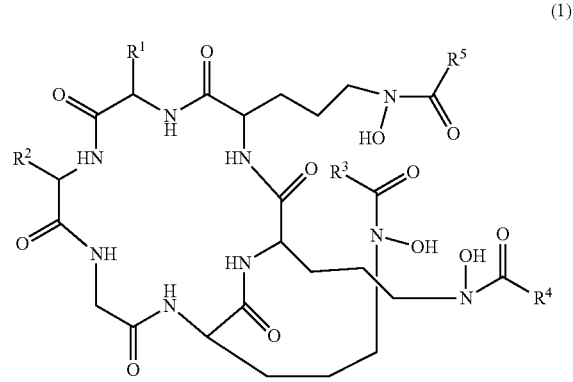

8 Claims, 20 Drawing Sheets

A. Caco2/bbe

B. SKCO1

C. SW620

A. Fraction

B. Ferrichrome

A. Caco2

B. SW620

A.

B.

1 Day after transplantation

9 Days after transplantation

A.

B.

C.

A.

B.

C.

A.

B.

C.

A.

B.

A.

B.

ANTITUMOR AGENT

CROSS-REFERENCE TO RELATED APPLICATIONS

This application is a U.S. national phase application of International Application No. PCT/JP2017/001803, filed Jan. 19, 2017 claiming the benefit of Japanese Application No. 2016-009224, filed Jan. 20, 2016, the contents of each of which are incorporated herein by their entireties for all purposes.

TECHNICAL FIELD

The present invention relates to an antitumor agent, in particular, an antitumor agent having a low risk of side effects and an excellent antitumor effect, and its use.

BACKGROUND ART

Colorectal cancer that develops in the large intestine (cecum, colon, rectum) is ranked third in males and first in females as a high-mortality cancer in Japan in 2014.

The cause of colorectal cancer remains to be determined. However, it has been pointed out that so-called Western-style dietary habit, including mainly eating meat, are associated with the development of colorectal cancer, as well as the intestinal environment, particularly an abnormal intestinal flora is associated with colorectal cancer (see, for example, Non-Patent Literatures 1 and 2). Some *Lactobacillus* or *Bifidobacterium* species, which are classified as good bacteria (probiotics), have also been reported to produce substances with an antitumor activity (see, for example, Non-Patent Literatures 3 and 4).

It has long been proposed and demonstrated that the intake of probiotics contributes to health maintenance or improvement with few adverse events. Therefore, it is expected that the discovery and use of useful ingredients having an antitumor activity derived from probiotics will lead to the provision of safe antitumor agents with fewer side effects and therapies for cancer using the same.

CITATION LIST

Non-Patent Literatures

Non-Patent Literature 1: Marchesi J R et al., PLoS One. 2011; 6(5): e20447.
Non-Patent Literature 2: Sobhani I et al., PLoS One. 2011 Jan. 27; 6(1): e16393.
Non-Patent Literature 3: Jan G et al., Cell Death Differ. 2002 February; 9(2): 179-88.
Non-Patent Literature 4: Cousin F J et al., PLoS One. 2012; 7(3): e31892.

SUMMARY OF INVENTION

Technical Problem

It is an object of the present invention to provide an antitumor agent which is highly safe and effective.

Solution to the Problem

The present inventors have found a substance having a high antitumor activity in the culture supernatant of *Lactobacillus* strains, and have completed the following inventions.

(1) An antitumor agent containing a compound represented by the following formula (1) or a complex thereof as an active ingredient,

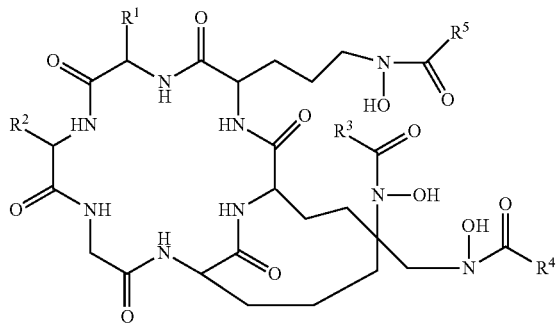

(1)

wherein $R^1$ represents a hydrogen atom or a hydroxymethyl group; $R^2$ represents a hydrogen atom, a methyl group, or a hydroxymethyl group; $R^3$, $R^4$, and $R^5$ each independently represent a methyl group, an $N^5$-(trans-5-hydroxy-3-methylpento-2-enoyl) group, an $N^5$-(cis-5-hydroxy-3-methylpento-2-enoyl) group, or an $N^5$-(trans-4-carboxy-3-methylpento-2-enoyl) group.

(2) The antitumor agent according to (1), wherein $R^1$ and $R^2$ are hydrogen atoms and $R^3$ to $R^5$ are methyl groups.

(3) The antitumor agent according to (1) or (2), wherein the tumor is gastrointestinal cancer.

Advantageous Effects of the Invention

The present invention makes it possible to provide a highly effective and safe antitumor agent that exhibits an antitumor activity equivalent to or better than that of 5-fluorouracil or cisplatin used in clinical practice as antitumor agents, while not causing adverse events such as hepatotoxicity.

DESCRIPTION OF THE EMBODIMENTS

Figure 1:
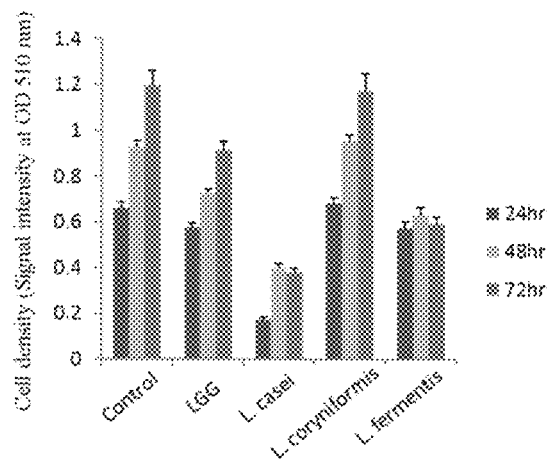
FIG. 1 illustrates graphs showing the antitumor activity of each culture supernatant of *Lactobacillus* strains *Lactobacillus* GG ATCC53103, *L. casei* ATCC334, *L. coryniformis* ATCC25600 and *L. fermentis* ATCC23271 against colorectal cancer cell lines. Panel A shows the antitumor activities against the colorectal cancer cell line Caco2/bbe, Panel B shows antitumor activities against the colorectal cancer cell line SKCO1, and Panel C shows antitumor activities against the colorectal cancer cell line SW620.
Figure 1:
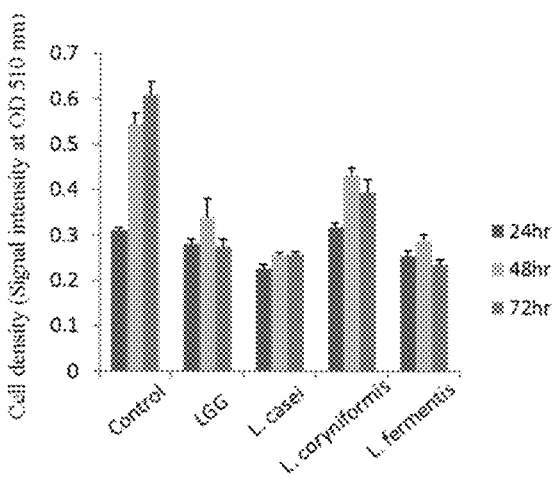
Figure 1:
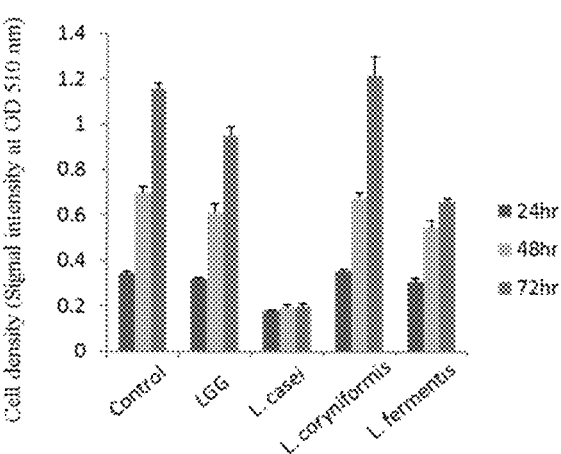

A first aspect of the present invention relates to an antitumor agent containing a compound represented by the following formula (1) or a complex thereof as an active ingredient,

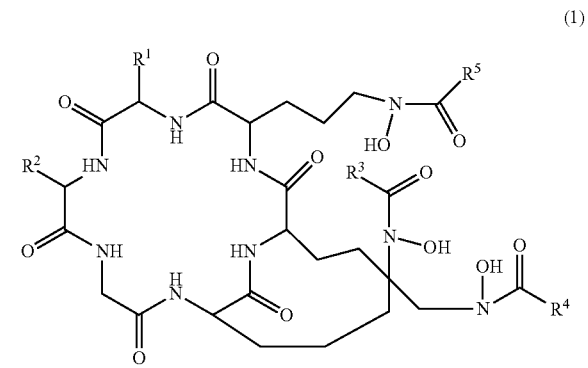

(1)

wherein $R^1$ represents a hydrogen atom or a hydroxymethyl group; $R^2$ represents a hydrogen atom, a methyl group, or a hydroxymethyl group; $R^3$, $R^4$, and $R^5$ each independently represent a methyl group, an N-(trans-5-hydroxy-3-methylpento-2-enoyl) group, an $N^5$-(cis-5-hydroxy-3-methylpento-2-enoyl) group, or an $N^5$-(trans-4-carboxy-3-methylpento-2-enoyl) group.

The compounds represented by the formula (1) are a kind of cyclic proteins, for example, reported in Patent Document 1 (JP 2009-28030 A), which are a kind of siderophores (chelating compounds derived from a microorganism forming a stable complex with an iron ion). The compounds represented by the formula (1) in which $R^1$ and $R^2$ are hydrogen atoms and $R^3$ to $R^5$ are all methyl groups are generally called ferrichromes. In Patent Document 1, the compounds represented by formula (1) are reported as siderophores produced by *Aspergillus oryzae*, which is a type of filamentous fungus.

The present inventors have confirmed that the culture supernatant of *Lactobacillus casei* (*L. casei*) ATCC334, which is a kind of probiotics registered and stored in American Type Culture Collection (ATCC), exhibits a strong antitumor activity against proliferation of various cancer cells such as colorectal, pancreatic, gastric and esophageal cancer cells, and that such activity is brought about by ferrichrome. Although More than 260 siderophores have been reported to date (SideroforeBase, http://bertrand-samuel.free.fr/siderophore_base/index.php), the antitumor activity of ferrichrome is a novel finding. Complexes with metal ions, especially iron ions, of the compounds represented by formula (1) are also included in the compounds used in the present invention.

The compounds represented by Formula (1) can be produced by culturing *Aspergillus oryzae* strain 3129-7 (FERM P-20961) under the culturing conditions described in Patent Document 1.

Ferrichromes can also be produced by culturing *L. casei*, in particular *L. casei* ATCC344, in a suitable medium. Preferably, ferrichromes can be produced by purification of a culture supernatant obtained by culturing *L. casei* ATCC344 in a medium suitable for culturing *Lactobacillus* bacteria, for example, a liquid medium such as Man Rogosa-Sharpe (MRS) broth (Difco) or Minimal Essential Media (Thermo Fisher Scientific), wherein the purification can be performed using gel-filtration, reverse phase chromatography, ion-exchange chromatography, and the like optionally combined as required. In addition, ferrichromes can also be chemically synthesized according to the methods described in Isowa (Bulletin of the Chemical Society of Japan 47(1), 215-220, 1974).

The compounds of formula (1), in particular ferrichrome, may be utilized as such as antitumor agents and may be utilized in the form of pharmaceutical compositions containing pharmaceutically acceptable buffers, stabilizers, preservatives, excipients and other components and/or other active components. Such a pharmaceutical composition is a second aspect of the present invention. Pharmaceutically acceptable components are well-known to those skilled in the art, and can be selected and used by those skilled in the art for example from those described in Japanese Pharmacopoeia, sixteenth edition or other written standard, within the scope of his/her normal implementation ability, depending on dosage forms.

The pharmaceutical composition comprising the antitumor agent of the present invention can be used in any form, and may be in the form of parenteral formulations, such as an injection and a drip, or in the form of oral formulations optionally with a suitable coating. Carriers that can be used in parenteral formulations include, for example, aqueous carriers such as saline or isotonic solutions containing glucose, D-sorbitol, and the like.

The method for administration of the antitumor agent of the present invention or the pharmaceutical composition containing the same is not particularly limited, but in the case of parenteral preparations, there can be exemplified, for example, intravascular administration, preferably intravenous administration, intraperitoneal administration, intestinal administration, subcutaneous administration, and the like. In one preferred embodiment, the therapeutic agent of the present invention is administered to a living body by intravenous administration or oral administration. The antitumor agent of the present invention or the pharmaceutical composition containing the same may be used in combination with other medicaments useful for the treatment of tumors.

The dosage of the antitumor agent of the present invention or the pharmaceutical composition containing the same can be appropriately selected depending on the dosage regimen, the age of the patient, the type of the disease, other conditions, and the like, and is usually 10 µg to 2000 µg, preferably 50 µg to 1000 µg, more preferably 100 µg to 500 µg per kg of body weight to an adult, and the antitumor agent or the pharmaceutical composition containing the same may be administered once or multiple times a day or intermittently.

Thus, the antitumor agent of the present invention or the pharmaceutical composition containing the same can be used for the prevention and/or treatment of a tumor, in particular gastrointestinal cancer, and therefore, a third aspect of the present invention can be said to also provide a method for the prevention and/or treatment of a tumor, in particular gastrointestinal cancer, using the compound of formula (1), in particular ferrichrome.

Detailed description of the present invention will be further made with reference to the following non-limiting Examples.

EXAMPLES

Cell Lines, Microorganisms and Cultures Thereof

Colorectal cancer cell lines Caco2/bbe (ATCC), SKCO-1 (ATCC) and SW620 (ATCC), pancreatic cancer cell lines bxpc3 (ATCC) and Suit2 (Health Science Research Resources Bank), gastric cancer cell lines MKN45 (National Institutes of Biomedical Innovation, Health and Nutrition JCRB Cell Bank) and SH-10-TC (Cell Resource Center for Biomedical Research Cell Bank), esophageal cancer cell line OE33 (DS Pharma), and rat intestinal epithelial cell line IEC-18 (ATCC) were used for evaluation.

Caco2/bbe, SKCO1 and Suit2 were cultured in DMEM, and SW620, BxPc3, MKN-45, SH-10-TC and OE33 were cultured in RPMI1640, both of which were supplemented with 10% FBS, 2 mM L-glutamine, 50 U/mL penicillin and 50 µg/mL streptomycin, respectively. IEC-18 was cultured in DMEM supplemented with 5% FBS, 1 U insulin, 2 mM L-glutamine, 50 U/mL penicillin, and 50 µg/mL streptomycin.

Mouse primary intestinal epithelial cells were prepared and cultured according to the method as reported previously (Liu X et al., Am J Pathol. 2012 February; 180(2): 599-607).

*L. casei* ATCC334, LGG ATCC53103, *L. coryniformis* ATCC25600 and *L. fermentis* ATCC23271 were purchased from ATCC. These microorganisms were cultured overnight at 37° C. using MRS broth (Difco) and then transferred to MEM and cultured for one day. The cultured medium was centrifuged at 5,000×g for 10 minutes to collect the supernatant, which was filtered through a 0.2 µm filter and used as the culture supernatant in the following examples.

Measurement of Antitumor Activity by SRB Assay

Test cells were dispensed into 96-well plates at $1.0 \times 10^4$ cells/well (n=5 unless otherwise specified), and incubated for 24 hours. Then the samples were added to the DMEM at a final concentration of 10 ng/mL to 10 µg/mL, incubated for 24 hours, 48 hours, 72 hours or 96 hours, and the plates were collected. After removing the medium, 5% TCA was added to each well, and the wells were left to stand at 4° C. for 1 hour, and washed 4 times with pure water. Plates were dried at room temperature and 100 µL of 0.057% by weight SRB aqueous solution was added to each well to stain the cells, washed 4 times with 0.1% acetic acid, and then dried. Cell densities at various incubation times were determined by measuring the OD at 510 nm of the stained cells dissolved in 10 mM Tris buffer.

Example 1

1) Antitumor Activity of Culture Supernatants

By using the colorectal cancer cell lines Caco2/bbe, SKCO-1 and SW620 as test cells and the culture supernatants of LGG ATCC53103, *L. casei* ATCC334, *L. coryniformis* ATCC25600 and *L. fermentis* ATCC23271 as measurement samples, an antitumor activity of each supernatant was measured by SRB-assay. The results are shown in FIG. 1. The culture supernatant of *L. casei* ATCC334 was found to have a strong antitumor activity against all of the colorectal cancer cell lines.

2) Purification of Antitumor Active Substance

A spin column with a 3 kDa molecular weight cut-off (GE Healthcare) was used to obtain fractions with a molecular weight of 3 kDa or less from the culture supernatant of *L. casei* ATCC334, and the fractions were then dialyzed using Micro Float-A-Lyzer Dialysis Device (Spectrum Laboratories) to collect fractions with a molecular weight of 0.5 kDa to 3 kDa.

The fractions with a molecular weight of 0.5 kDa to 3 kDa were subjected to gel-filtration chromatography using AKTA-HPLC (GE Healthcare) equipped with Superdex peptide column, and the fractions in which antitumor activities were confirmed were collected.

The collected fractions were subjected to reverse phase HPLC (linear gradients of 0.1% formic acid and 0.1% formic acid/acetonitrile) using L-column (Chemicals Evaluation and Research Institute) to collect antitumor active fractions.

Figure 2:
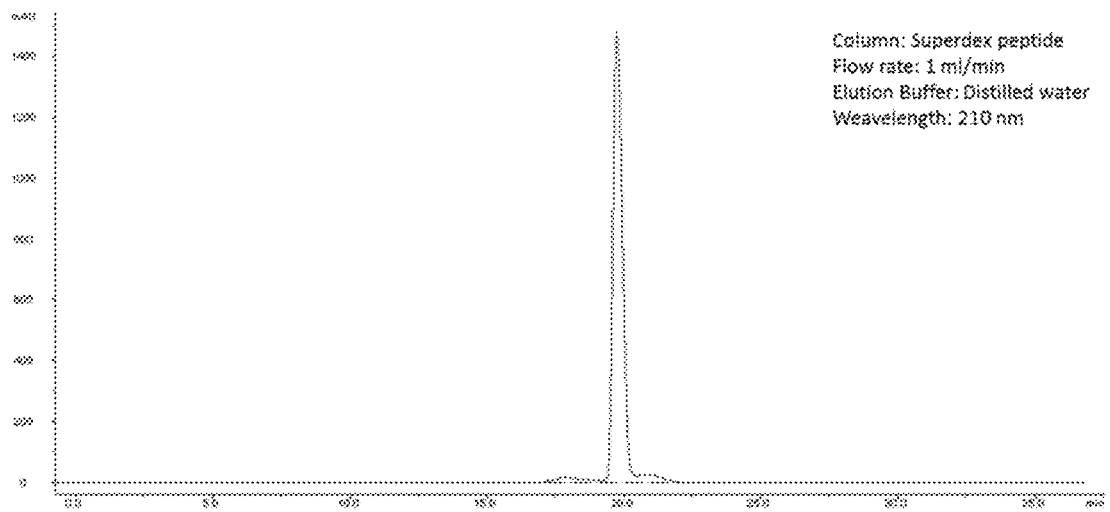
FIG. 2 illustrates a HPLC chromatographic chart of a compound exhibiting an antitumor activity purified from a culture supernatant of *L. casei* ATCC334.

In addition, ion-exchange chromatography using each of HiTrap-DEAE, CM and SP columns (all GE Healthcare), was performed. in this order to collect the antitumor active fractions. In addition, normal phase chromatography using a ZIC-HILIC column (Merck Millipore) was performed to collect an antitumor active fraction containing a compound exhibiting a single peak in HPLC (FIG. 2).

The protease treatment was performed on the antitumor active fraction finally obtained, but no change was observed in the antitumor activity. In addition, amino acid analysis, sugar chain analysis, and peptidoglycan detection were attempted, but none of the amino acid, sugar chain, and peptidoglycan were detected. Further atomic absorption spectroscopy was attempted, and iron, zinc and calcium were detected.

Figure 3:
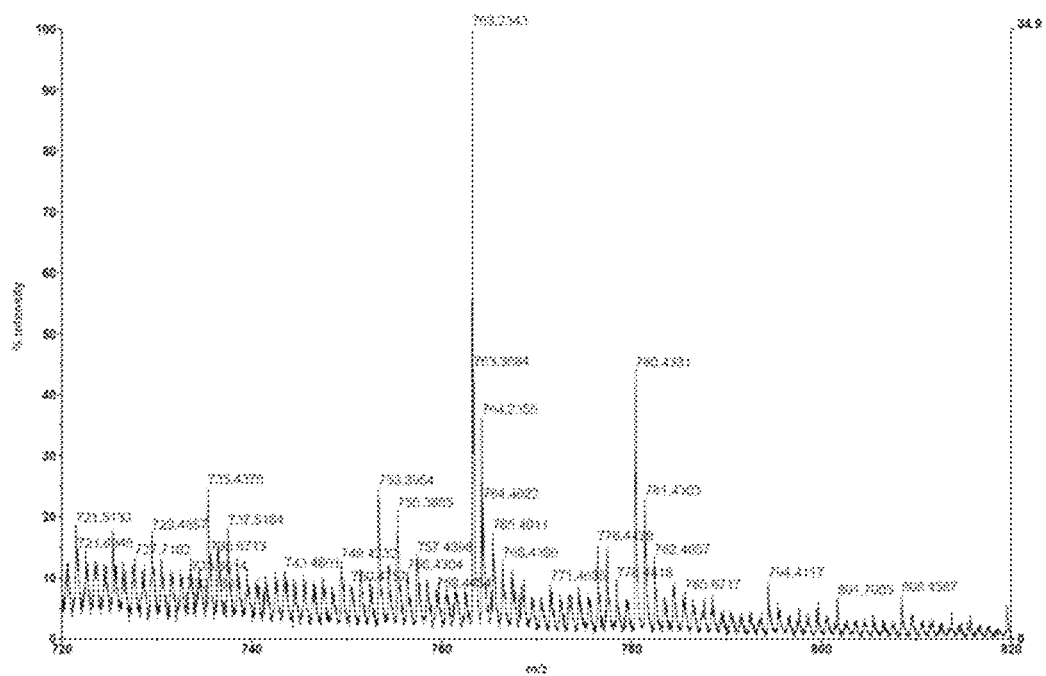
FIG. 3 illustrates charts showing mass spectrometry results of the purified fraction exhibiting an antitumor activity (Panel A), and of commercial ferrichrome (Panel B).
Figure 3:
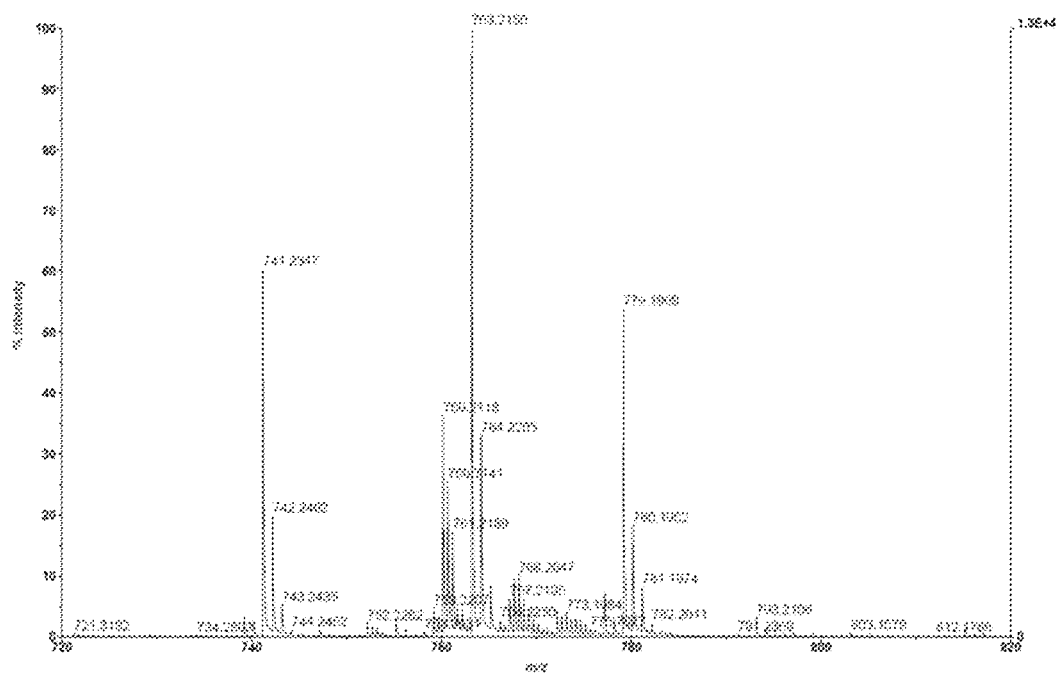

This fraction was subjected to mass spectrometry (TOF, ionization method: micro ESI) using Nano Frontier elD Liquid Chromatograpy Mass Spectrometer (Hitachi High-technologies), and a chart shown in FIG. 3A was obtained. The peak at m/z 763.2 in this chart was approximately consistent with that in the chart obtained for commercial ferrichrome (Sigma-Aldrich) by mass spectrometry in a similar mannar (FIG. 3B). By using commercially available ferrichrome as a measurement sample and the colorectal cancer cell line SW620 as a test cell, an antitumor activity was measured. Ferrichrome was confirmed to have a strong antitumor activity.

From the above, the antitumor active compound contained in the culture supernatant of *L. casei* ATCC334 was identified as ferrichrome.

Example 2

Figure 4:
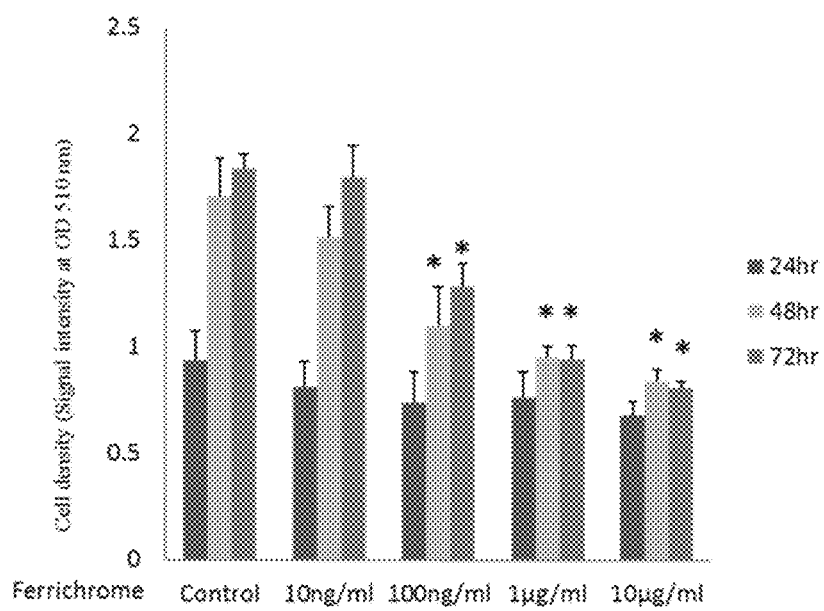
FIG. 4 illustrates graphs showing the dose-dependency of the antitumor activity of ferrichrome against the colorectal cancer cell line Caco2/bbe (Panel A) and the colorectal cancer cell line SW620 (Panel B).
Figure 4:
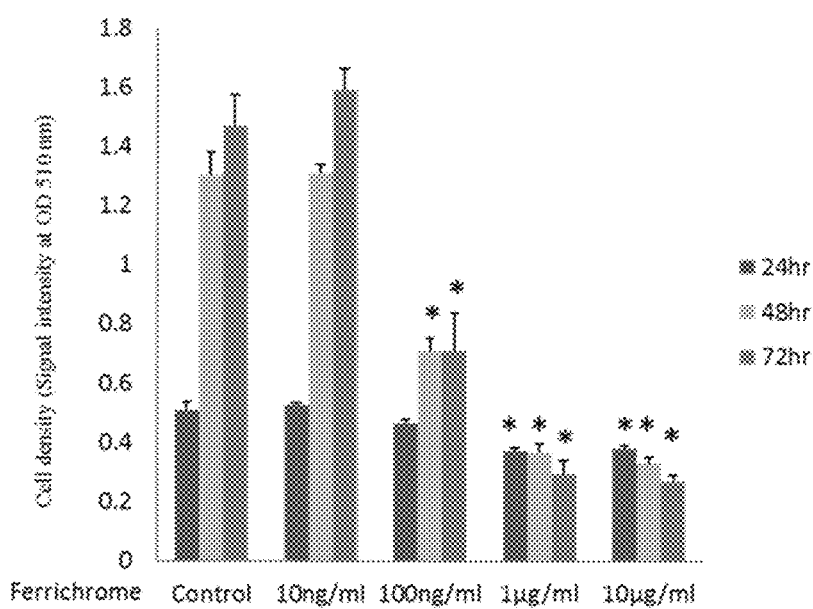
Figure 5:
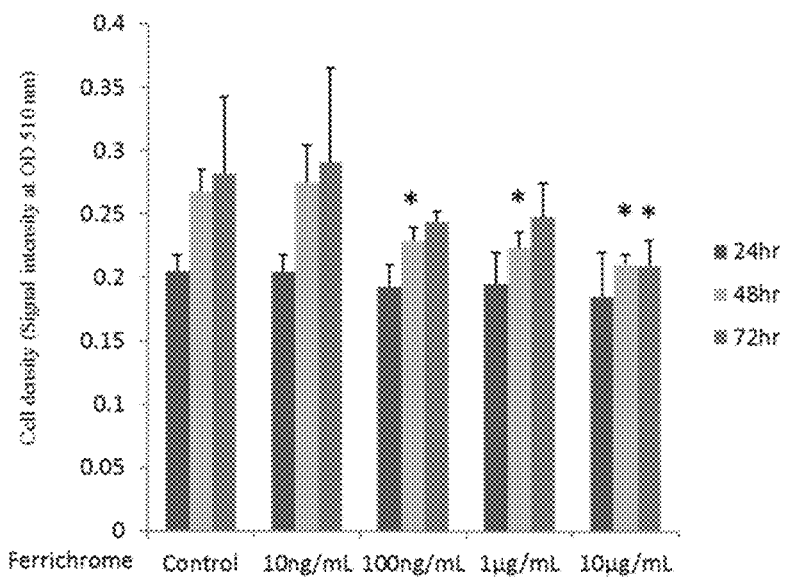
FIG. 5 illustrates graphs showing the effect of ferrichrome on rat intestinal epithelial cells IEC-18 (Panel A) and mouse primary intestinal epithelial cells (Panel B).
Figure 5:
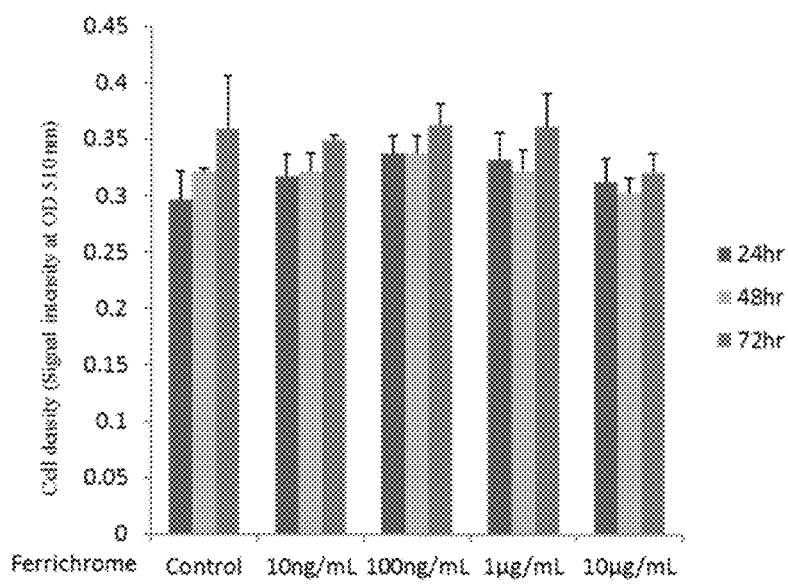

The dose-dependency of the antitumor activity of ferrichrome was examined by SRB-assay using Caco2/bbe and SW620 as test cells. At the same time, the effects of ferrichrome on rat intestinal epithelial cell line IEC-18 and mouse primary intestinal epithelial cells were investigated. The results confirmed that ferrichrome exhibited a dose-dependent antitumor activity against Caco2/bbe and SW620 (FIG. 4), while not significantly reducing cell densities of IEC-18 and mouse primary intestinal epithelial cells (FIG. 5), and that ferrichrome exhibited an antitumor activity against other colorectal cancer cell lines HT29, HCT116 and SKCO1 in a similar manner to those against Caco2/bbe and SW620.

Example 3

Figure 6:
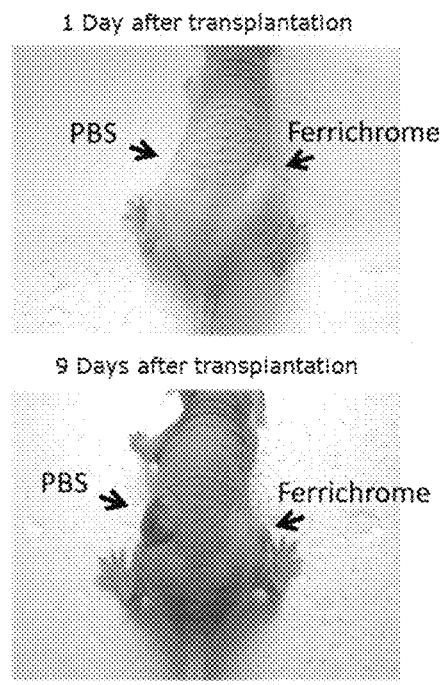
FIG. 6 illustrates photographs showing the tumor mass growth in nude mice transplanted with the colorectal cancer cell line SW620, to which ferrichrome was administered. A photograph 1 day after transplantation is shown above and a photograph 9 days after transplantation is shown below.
Figure 7:
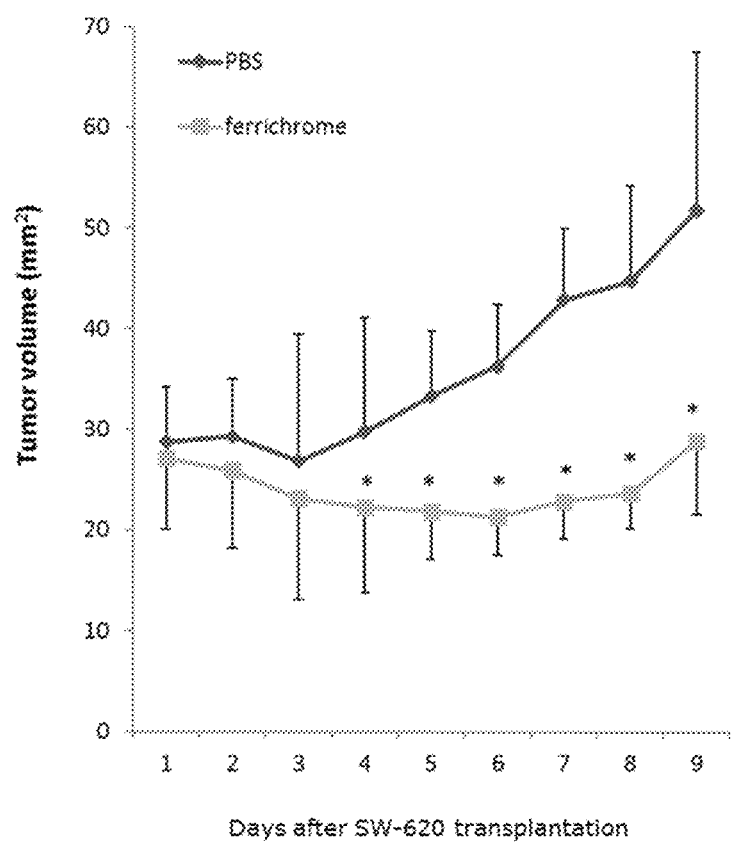
FIG. 7 illustrates a graph showing the change in tumor mass volume in nude mice transplanted with the colorectal cancer cell line SW620, to which ferrichrome was administered.

$2 \times 10^6$ cells of colorectal cancer cell line SW620 were transplanted subcutaneously into the back of BALB/c-nude mice. Daily from the day following transplantation, 10 µg/day of ferrichrome (n=16) or PBS (n=16) was administered to the transplantation sites and the growth of the tumor mass at each transplantation site was observed for 9 days. The appearance of the mice on day 1 after transplantation and on day 9 after transplantation are shown in FIG. 6, and the change in tumor mass volume is shown in FIG. 7, respectively. As shown in FIGS. 6 and 7, ferrichrome markedly inhibited the growth of the tumor mass from transplanted cells.

Example 4

Figure 8:
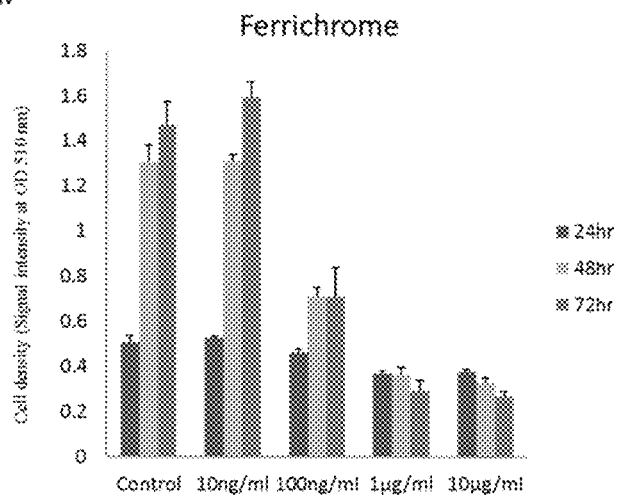
FIG. 8 illustrates graphs showing the comparison of the antitumor effects of ferrichrome (Panel A), 5-fluorouracil (Panel B) and cisplatin (Panel C) on the colorectal cancer cell line SW620.
Figure 8:
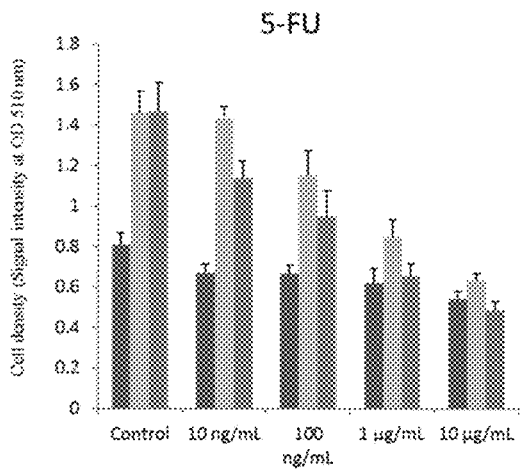
Figure 8:
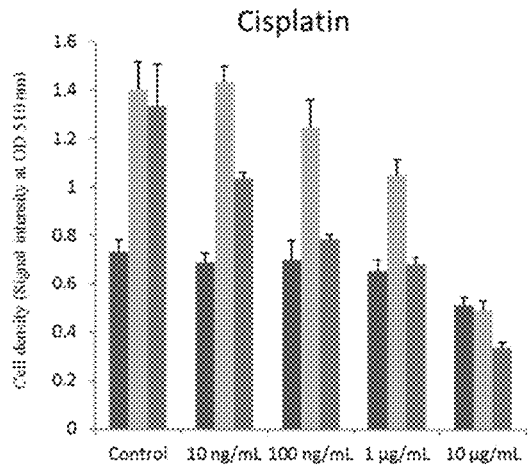
Figure 9:
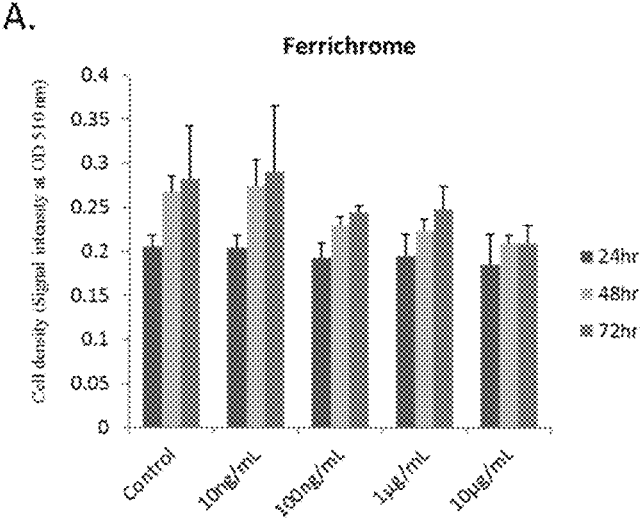
FIG. 9 illustrates graphs showing the comparison of the effects of ferrichrome (Panel A), 5-fluorouracil (Panel B) and cisplatin (Panel C) on rat intestinal epithelial cells IEC-18.
Figure 9:
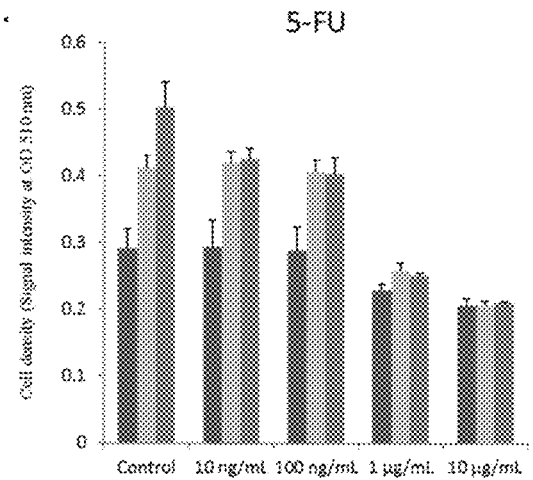
Figure 9:
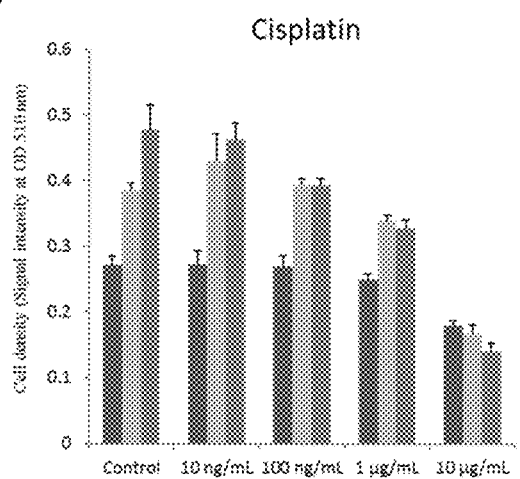

The antitumor activities were compared by SRB assays using the colorectal cancer cell line SW620 and the intestinal epithelial cell IEC-18 as test cells and ferrichrome, 5-fluorouracil (5-FU), which is used as an anticancer agent, and cisplatin as measurement samples. The results confirmed that ferrichrome exhibited a higher antitumor activity against SW620 than those of 5-FU and cisplatin (FIG. 8), and that 5-FU and cisplatin reduced a cell density for IEC-18, particularly when used at high concentrations, while ferrichrome did not significantly affect the cell density (FIG. 9).

Test Example 1

Figure 10:
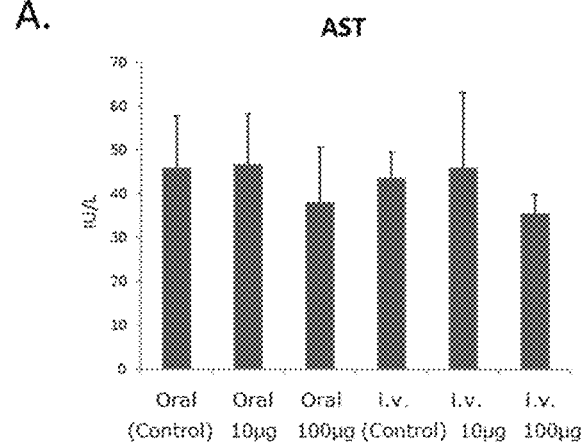
FIG. 10 illustrates graphs showing the measurement results of blood AST (Panel A), ALT (Panel B) and serum iron (Panel C) in mice to which ferrichrome was orally or intravenously administered.
Figure 10:
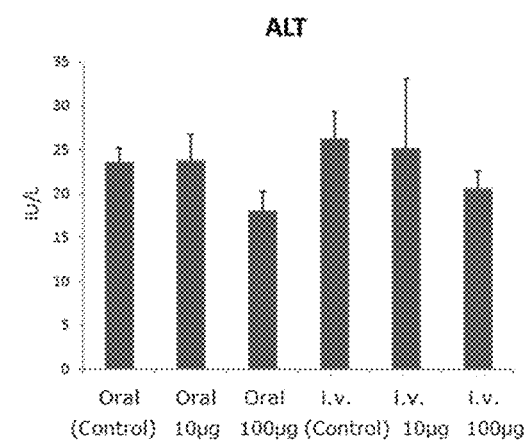
Figure 10:
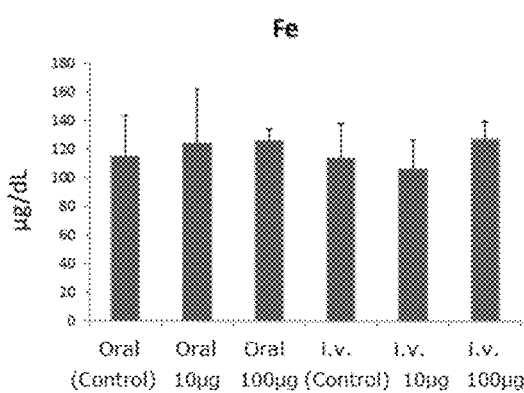

Blood AST (aspartate aminotransferase), ALT (alanine aminotransferase), and serum iron were measured in C57/BL6 mice (n=5) after oral or intravenous administration of 10 µg or 100 µg of ferrichrome/day for 7 days. No significant changes were observed compared with controls (FIG. 10).

Test Example 2

Figure 11:
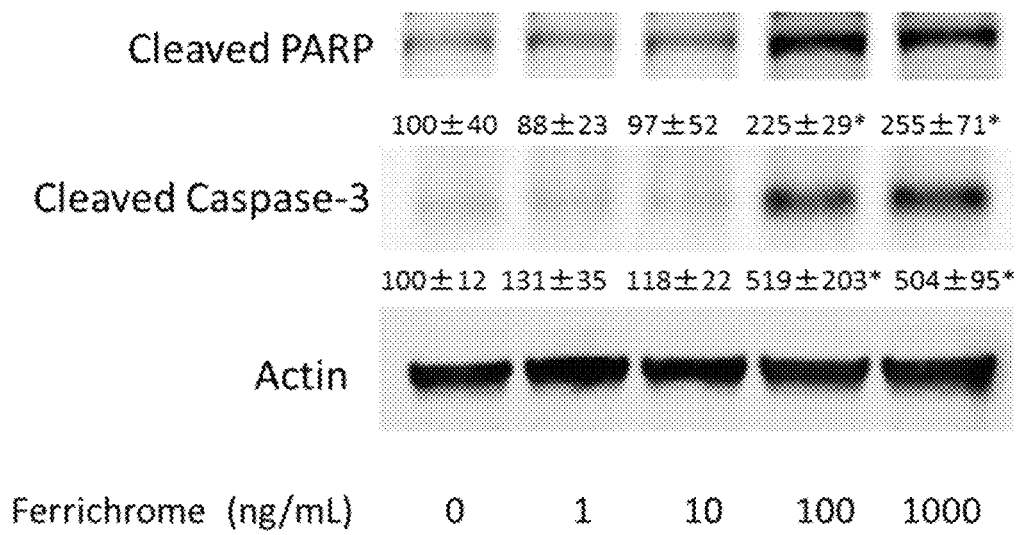
FIG. 11 illustrates a photograph showing the result of Western blotting for the expression of cleaved caspase-3 and PARP in the colorectal cancer cell line SW620 treated with ferrichrome.
Figure 12:
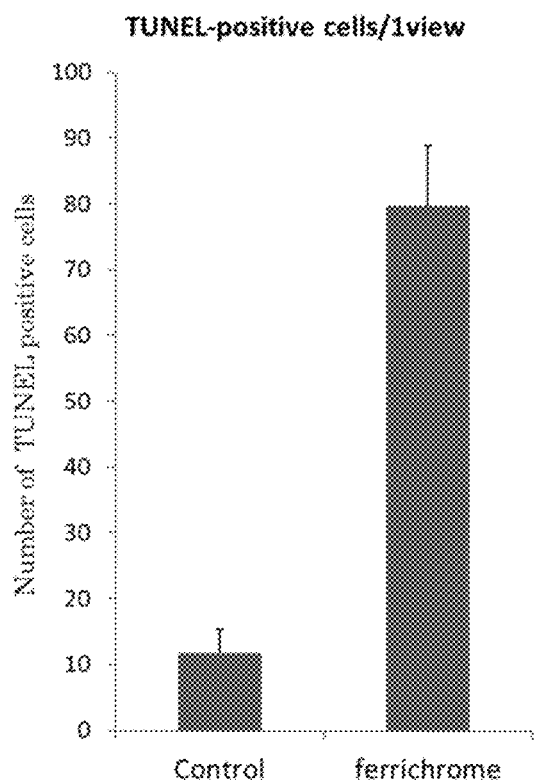
FIG. 12 illustrates a graph showing the number of TUNEL stain-positive cells in the colorectal cancer cell line SW620 treated with 0.1 µg/mL ferrichrome.

Total proteins recovered from the ferrichrome-treated colorectal cancer cell line SW620 using mammalian cell extraction kit (BioVision) were subjected to Western blotting using specific antibodies for cleaved caspase-3 and PARP (Cell Signaling), respectively. The results confirmed that cleaved caspase-3 and PARP increased dose-dependently by addition of ferrichrome, and that apoptosis was induced (FIG. 11). The induction of apoptosis was also confirmed by TUNEL staining (In Situ Cell Death Detection Kit and TMR red (Roche Diagnostic)). FIG. 12 shows the results of TUNEL stain-positive cells in the SW620 treated with 0.1 µg/mL ferrichrome.

Figure 13:
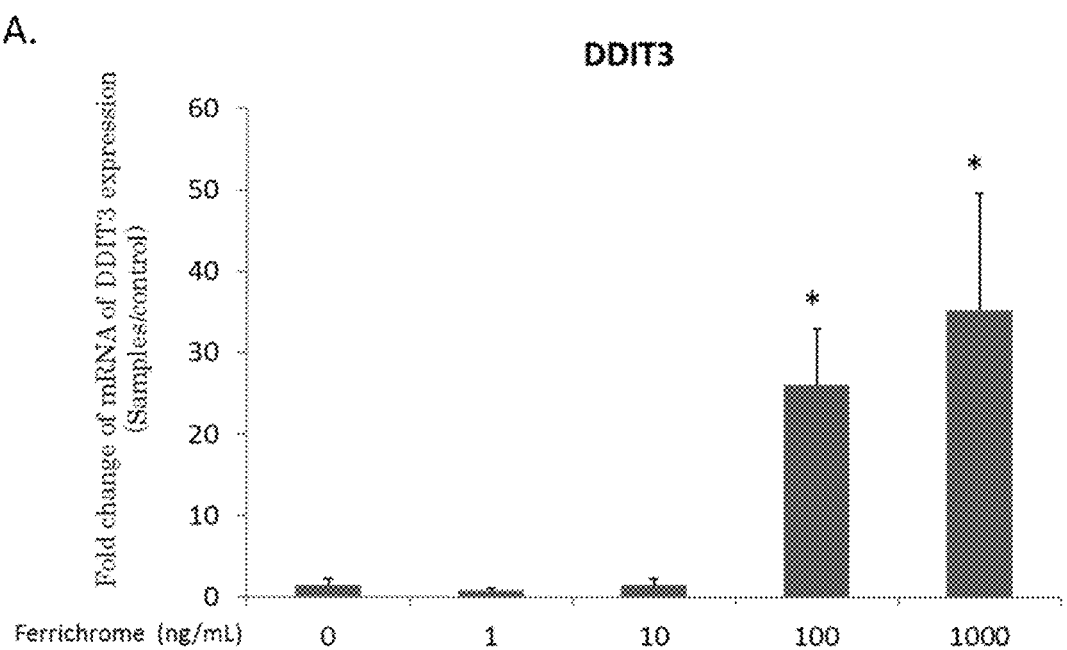
FIG. 13 illustrates the results of RT-PCR (Panel A) and Western blotting photograph (Panel B) showing the increased expression of DDIT3 in the colorectal cancer cell line SW620 treated with ferrichrome.
Figure 13:
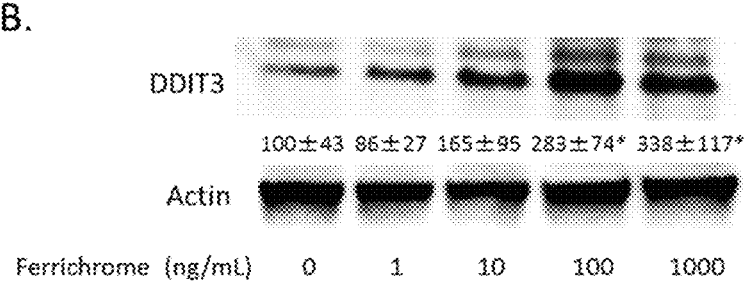

Changes in mRNA expression between ferrichrome-treated and untreated colorectal cancer cell line SW620 were measured by high-throughput sequence analysis using a MetaCore software program. The results confirmed that the expression of the genes involved in the endoplasmic reticulum stress were changed by ferrichrome treatment, and in particular, a remarkable change (increase in expression) of the expression level of DNA damage-inducible transcript 3 (DDIT3) was observed. DDIT3 is a protein known to be involved in Bax-Bak mitochondrial permeation and JNK signaling (Tabas I, Ron D. Nat Cell Biol. 2011 March; 13(3): 184-90). The enhanced expression of DDIT3 was also confirmed by RT-PCR and Western blotting (FIG. 13).

Figure 14:
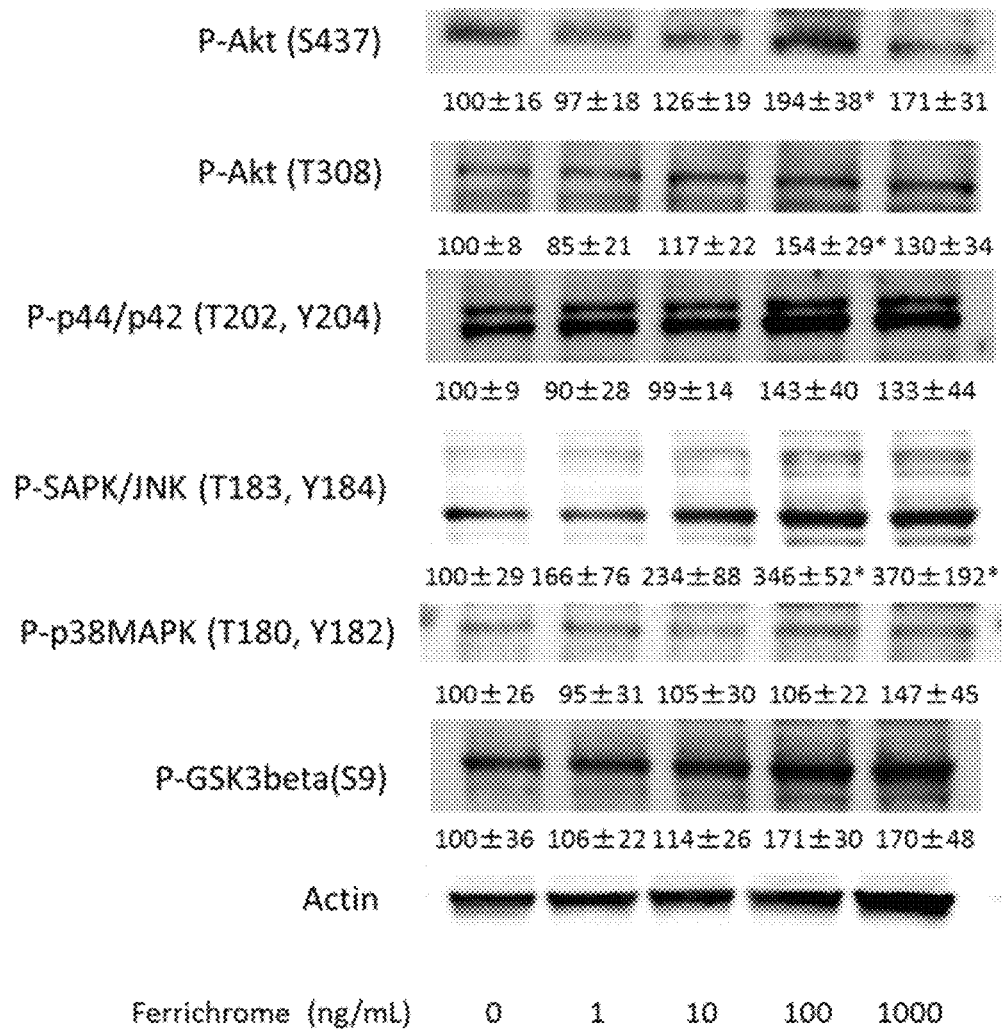
FIG. 14 illustrates a photograph showing the results of Western blotting for the expression of phospho-Akt, JNK, ERK, p38 MAPK and GSK3β in the colorectal cancer cell line SW620 treated with ferrichrome.
Figure 15:
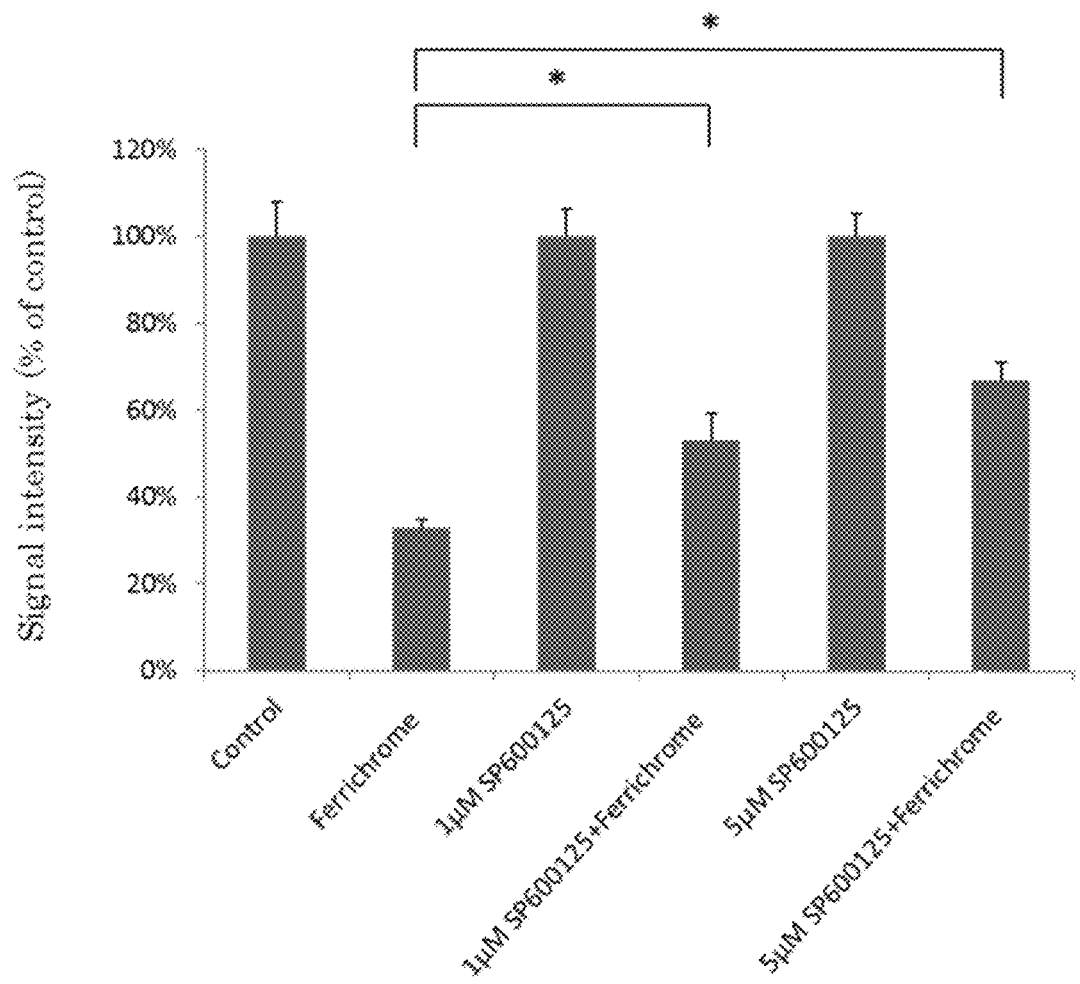
FIG. 15 illustrates a graph showing the change in the antitumor activity against the colorectal cancer cell line SW620 to which SP600125, an inhibitor of the JNK pathway, is added together with ferrichrome.

In addition, Western blotting of total proteins recovered from ferrichrome-treated SW620 with specific antibodies (Cell Signaling) against phospho-Akt, JNK, ERK, p38 MAPK, and GSK3β, respectively, confirmed that the expression of phosphorylated JNK in SW620 was increased (FIG. 14), and when both ferrichrome (0.1 μg/mL) and SP600125 (1 or 5 μM), an inhibitor of the JNK pathway, were added to SW620, suppression of the antitumor activity of ferrichrome was observed (FIG. 15), and the expression of cleaved caspase-3 and PARP were also confirmed. This decreased expression of cleaved caspase-3 and PARP was also observed when ferrichrome-added SW620 was treated with siRNA to JNK.

From the above results, it was inferred that the reduction in cell density of SW620 by addition of ferrichrome was caused by the activation of the apoptotic pathway involving JNK-DDIT3.

Example 5

Figure 16:
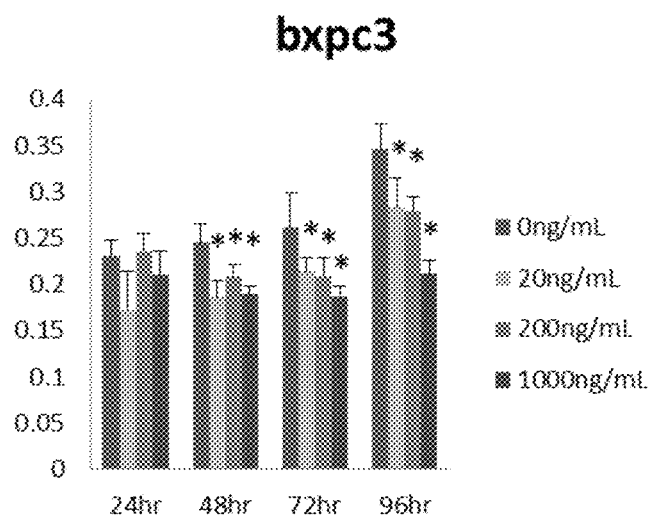
FIG. 16 illustrates graphs showing the dose-dependency of the antitumor activity of ferrichrome against the pancreatic cancer cell lines bxpc3 and suit2. The vertical axis represents the cell density (OD at 510 nm) and the horizontal axis represents the culture time after ferrichrome addition.
Figure 16:
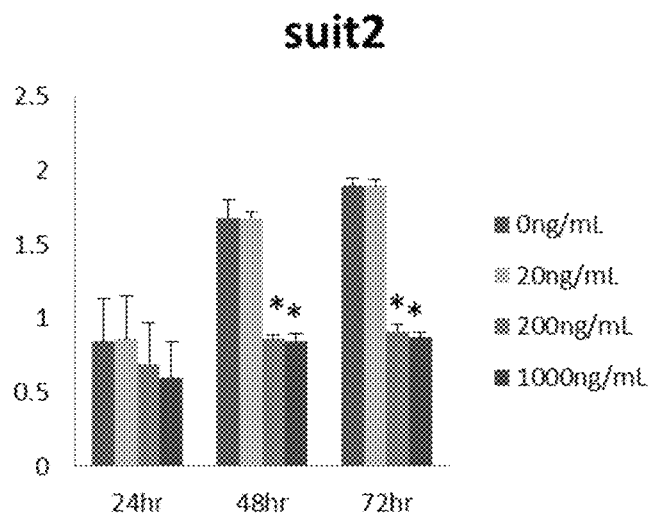
Figure 17:
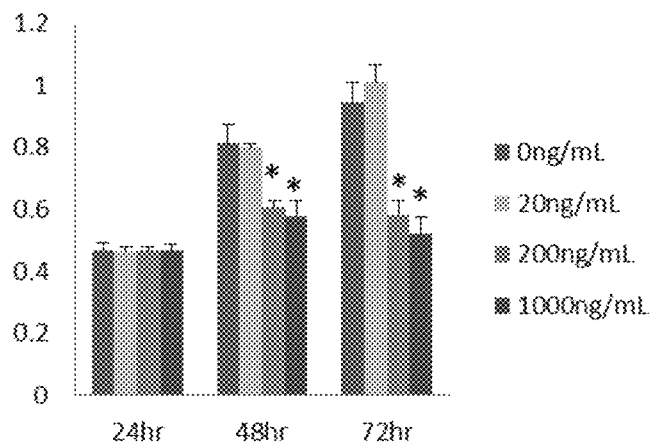
FIG. 17 illustrates graphs showing the dose-dependency of the antitumor activity of ferrichrome against the gastric cancer cell lines MKN45 and SH-10-TC. The vertical axis represents the cell density (OD at 510 nm) and the horizontal axis represents the culture time after ferrichrome addition.
Figure 17:
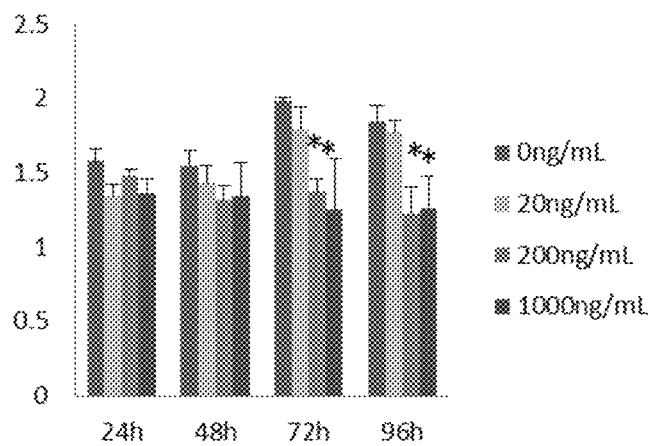
Figure 18:
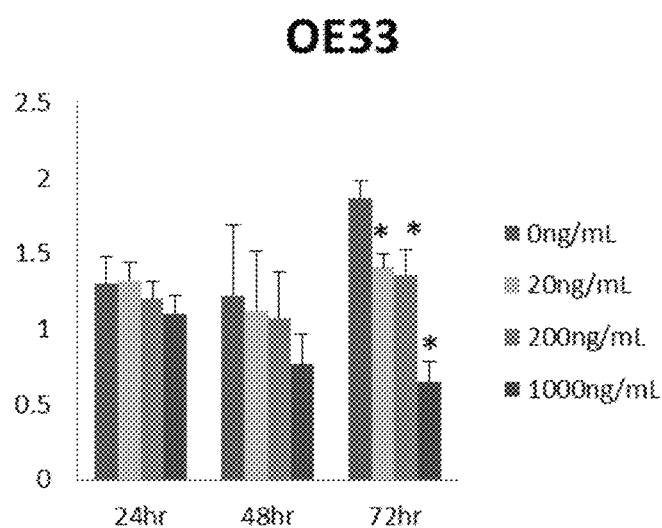
FIG. 18 illustrates a graph showing the dose-dependency of the antitumor activity of ferrichrome against the esophageal cancer cell line OE33. The vertical axis represents the cell density (OD at 510 nm) and the horizontal axis represents the culture time after ferrichrome addition.

By using the pancreatic cancer cell lines bxpc3 and suit2, the gastric cancer cell lines MKN45 and SH-10-TC, and the esophageal cancer cell line OE33 as test cells, the dose-dependency of the antitumor activity of ferrichrome was examined by SRB-assay. Ferrichrome exhibited a dose-dependent antitumor activity against all test cells (FIGS. 16-18). Ferrichrome was found to exhibit an antitumor activity against other pancreatic cancer cell lines (KP3, KP1N, KP3L, Miapaca), gastric cancer cell lines (MKN7, MKN74), and esophageal cancer cell line (OE19) similarly.

Example 6

Figure 19:
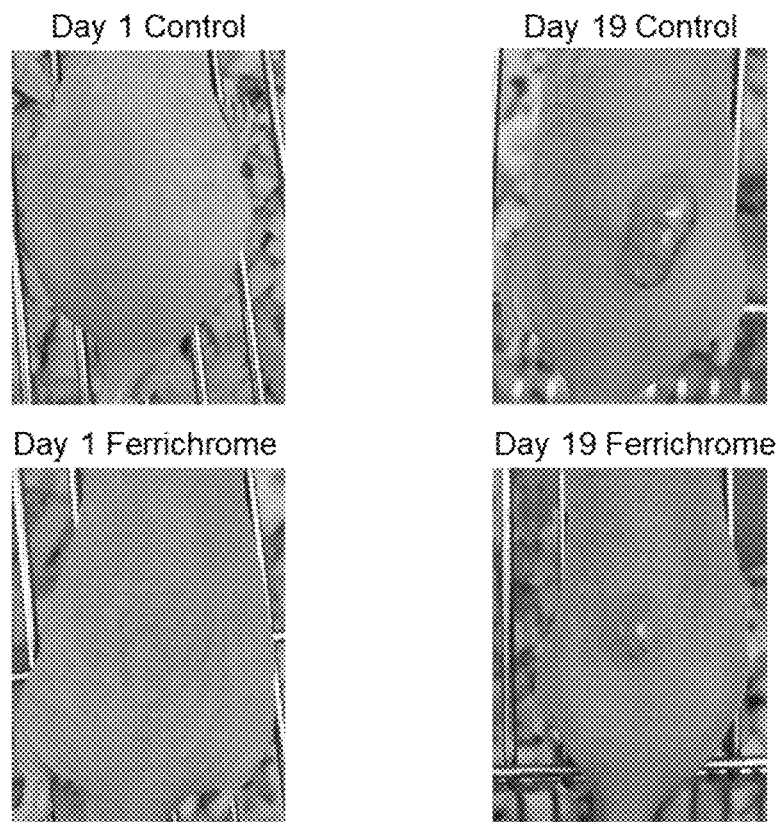
FIG. 19 illustrates photographs showing the tumor mass growth in nude mice transplanted with the gastric cancer cell line MKN45, to which ferrichrome was administered.
Figure 20:
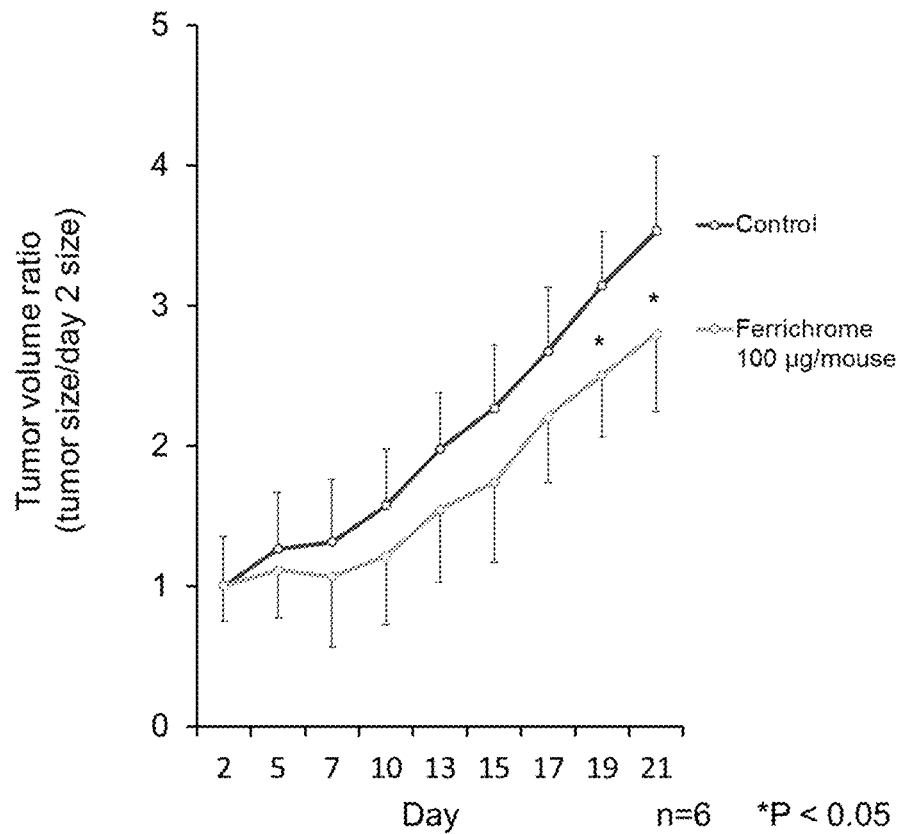
FIG. 20 illustrates a graph showing the change in tumor volume ratio in mice transplanted with the gastric cancer cell line MKN45, to which ferrichrome was administered.

Two groups of BALB/c nude mice (n=6/group) were transplanted with 1×10⁶ gastric cancer cells MKN45 by subcutaneous injection into their back. Each day from the day following transplantation, 100 μg of ferrichrome dissolved in PBS in one group and PBS alone in the other group were administered into the transplantation site, and the mice were kept under normal breeding conditions for 21 days. Photographs of the transplantation site 1 day and 19 days after transplantation are shown in FIG. 19, and the change in tumor volume ratio when the tumor volume 1 day after transplantation set to 1 is shown in FIG. 20.

The increased tumor volume ratio in mice administered ferrichrome was suppressed compared with that of the control group administered PBS alone, and the tumor mass size at the transplantation site was reduced to such an extent that it could be clearly distinguished by the naked eye.

Example 7

Figure 21:
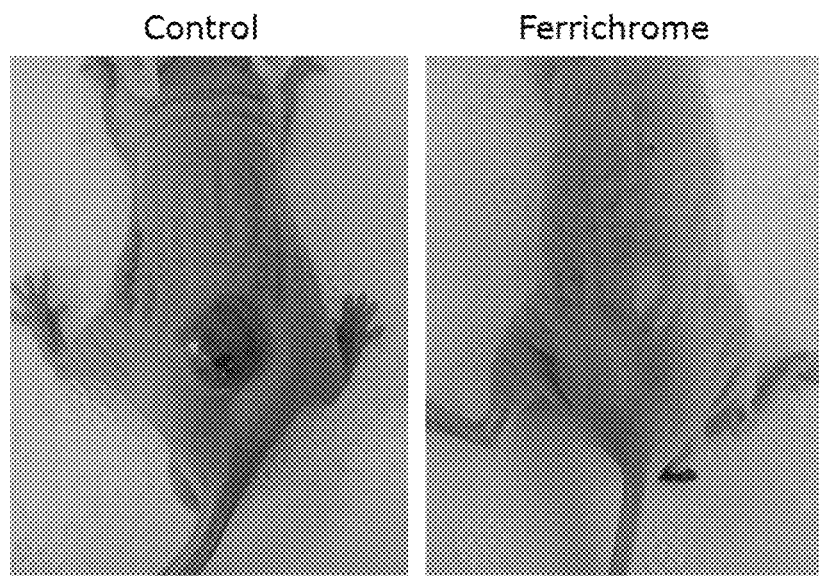
FIG. 21 illustrates photographs showing the tumor mass 12 days after cancer cell transplantation in nude mice transplanted with the pancreatic cancer cell line Suit2, to which ferrichrome was administered.
Figure 22:
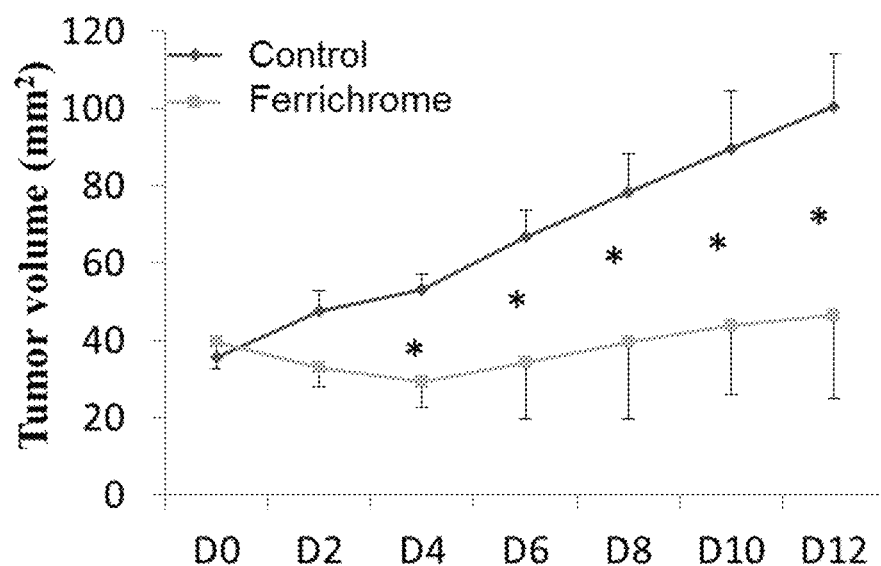
FIG. 22 illustrates a graph showing the change in tumor mass volume in nude mice transplanted with the pancreatic cancer cell line Suit2, to which ferrichrome was administered.

Two days after subcutaneous transplantation of 1×10⁶ pancreatic cancer cell Suit2 in two groups of nude mice (n=5/group), 100 μg of ferrichrome dissolved in PBS in one group and PBS alone in the other group were administered intraperitoneally once every two days for 12 days under normal breeding Conditions. A photograph of the transplantation site 12 days after transplantation is shown in FIG. 21, and the change in volume of the tumor mass is shown in FIG. 22.

The increase in tumor volume in mice administered ferrichrome intraperitoneally was markedly suppressed compared with that in the control group administered PBS alone.

Example 8

Azoxymethane (AOM) was administered intraperitoneally at 10 mg/kg to BALB/c mice (6 weeks old, male). Following 1 week breeding after AOM treatment, mice were administered drinking water containing dextran sulfate sodium (DSS, MP bio) diluted to 1.5% with distilled water by free access for 1 week. After a 1-week wash-out period, mice were administered drinking water containing dextran sulfate sodium (DSS, MP bio) diluted to 1% with distilled water by free access for 1 week, to prepare chemical carcinogenic models. After one more 1-week wash-out period, 50 μg of ferrichrome diluted in PBS was orally administered daily for 28 days under normal breeding conditions. After breeding, the large intestine was taken out from the mice and the tumor area was measured.

Figure 23:
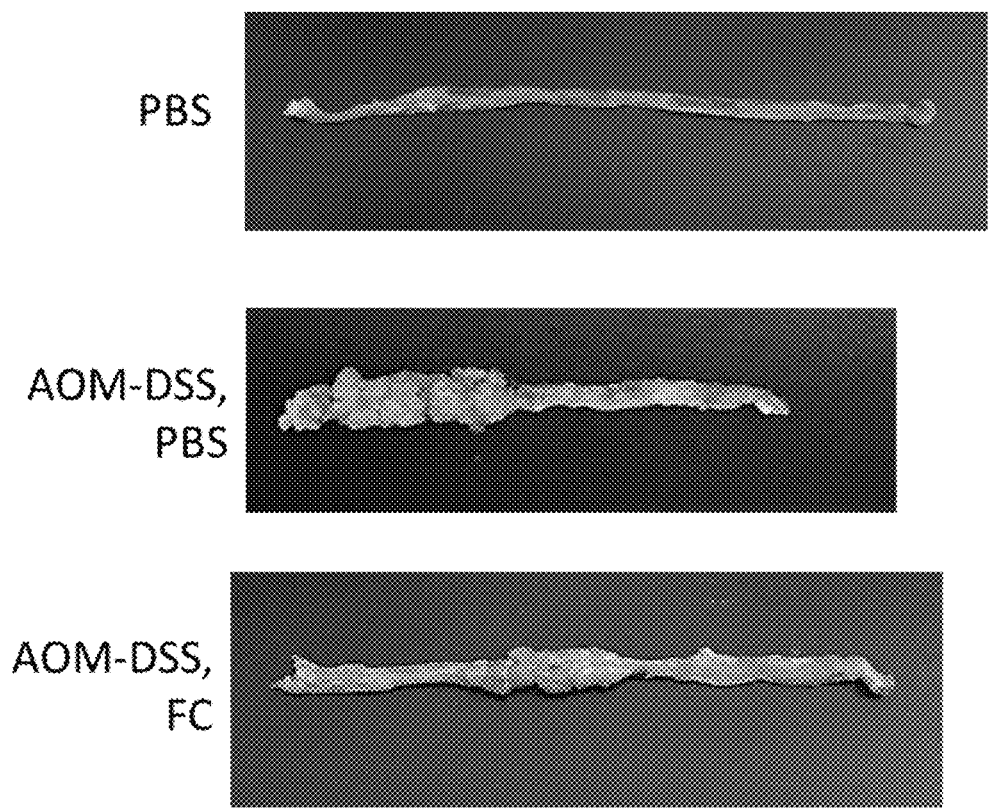
FIG. 23 illustrates photographs of colons taken out from normal mice orally administered PBS (PBS), chemical carcinogenic mice orally administered PBS (AOM-DSS, PBS), and chemical carcinogenic mice orally administered ferrichrome (AOM-DSS, FC).
Figure 24:
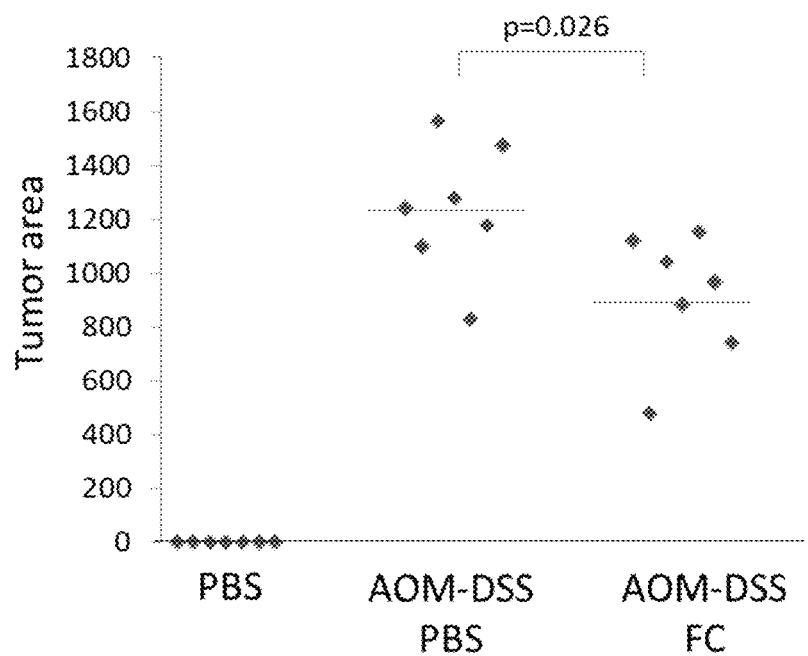
FIG. 24 illustrates a graph showing the tumor areas in the large intestine of normal mice orally administered PBS (PBS), chemical carcinogenic mice orally administered PBS (AOM-DSS, PBS), and chemical carcinogenic mice orally administered ferrichrome (AOM-DSS, FC).

Normal mice not administered AOM and DSS and chemical carcinogenic mice orally administered PBS alone were prepared, respectively, and the tumor area in the large intestine was measured in the same manner. Photographs showing the appearance of the large intestine in each mouse are shown in FIG. 23, and tumor areas in the large intestine are shown in FIG. 24.

The tumor area in the large intestine of chemical carcinogenic mice orally administered ferrichrome (n=7) was significantly suppressed compared with that of chemical carcinogenic mice administered PBS alone (n=7).

Example 9

Azoxymethane (AOM) was administered intraperitoneally at 10 mg/kg to BALB/c mice (6 weeks old, male). Following 1 week breeding after AOM treatment, mice were administered drinking water containing dextran sulfate sodium (DSS, MP bio) diluted to 1% with distilled water by free access for 1 week. After a 1-week wash-out period, 100 μg of ferrichrome dissolved in PBS was intraperitoneally administered once every 2 days for 49 days under normal breeding conditions. After breeding, the large intestine was taken out from the mice and the tumor area was measured.

Figure 25:
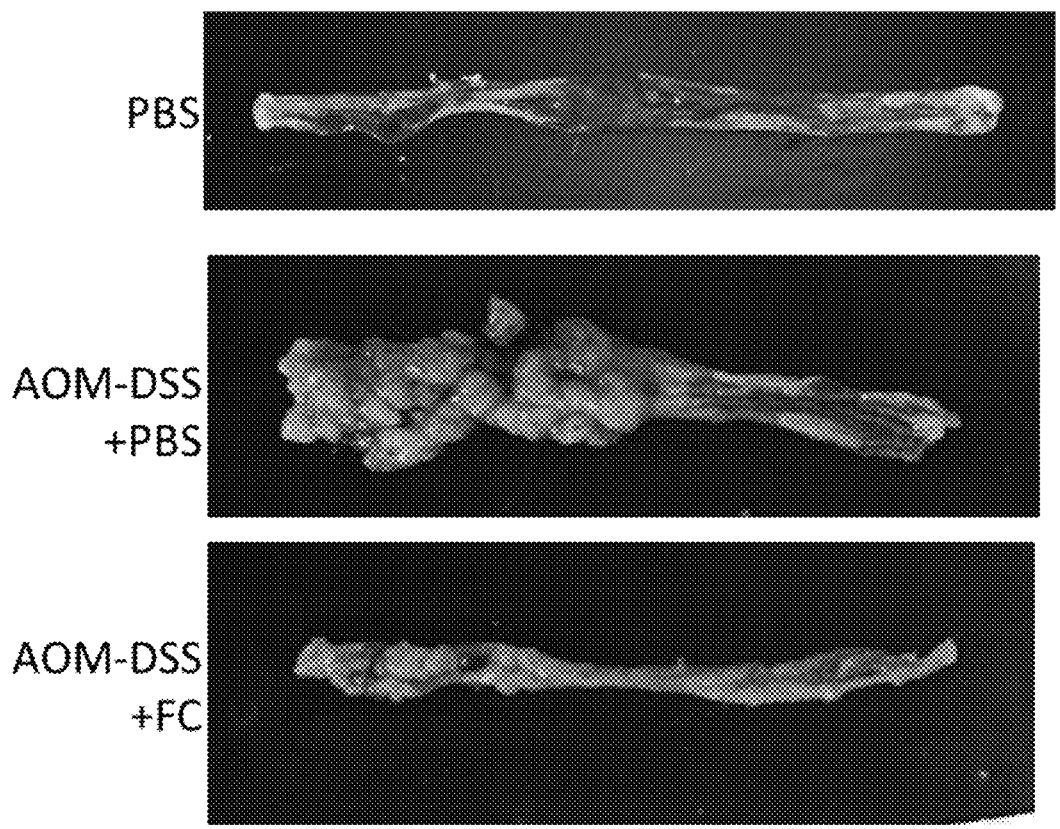
FIG. 25 illustrates photographs of colons taken out from normal mice intraperitoneally administered PBS (PBS), chemical carcinogenic mice intraperitoneally administered PBS (AOM-DSS, PBS), and chemical carcinogenic mice intraperitoneally administered ferrichrome (AOM-DSS, FC).
Figure 26:
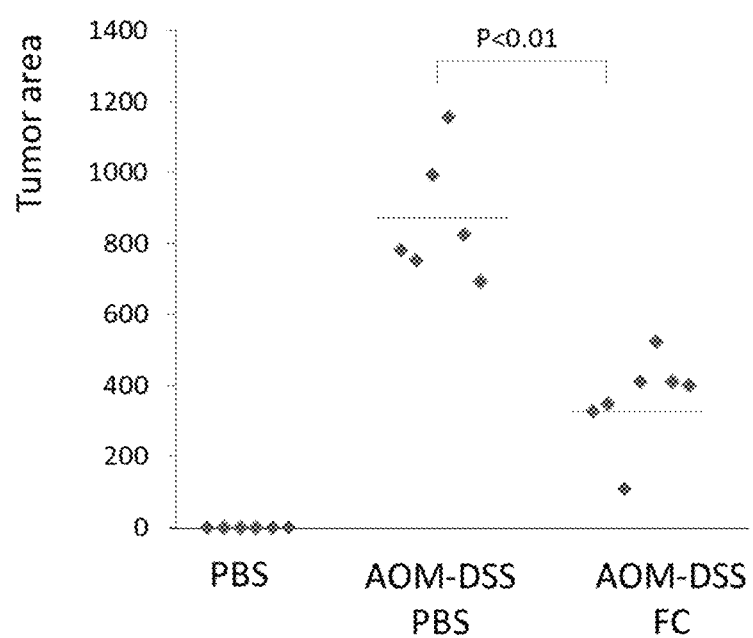
FIG. 26 illustrates a graph showing the tumor areas in the large intestine of normal mice intraperitoneally administered PBS (PBS), chemical carcinogenic mice intraperitoneally administered PBS (AOM-DSS, PBS), and chemical carcinogenic mice intraperitoneally administered ferrichrome (AOM-DSS, FC).

Normal mice not administered AOM and DSS and chemical carcinogenic mice intraperitoneally administered PBS alone were prepared, respectively, and the tumor area in the large intestine was measured in the same manner. Photographs showing the appearance of the large intestine in each mouse are shown in FIG. 25, and tumor areas in the large intestine are shown in FIG. 26.

The tumor area in the large intestine of chemical carcinogenic mice intraperitoneally administered ferrichrome (n=7) was significantly suppressed compared with that of chemical carcinogenic mice administered PBS alone (n=6).

INDUSTRIAL APPLICABILITY

The antitumor agent of the present invention has industrial applicability in the manufacture of a medicament.

The invention claimed is:
1. A method for treating a tumor in a subject in need thereof, comprising administrating the subject a compound represented by the following formula (1) or a complex thereof with a metal ion in an amount of 10-2000 μg per kg of body weight of the subject,

[Formula 1]

(1)

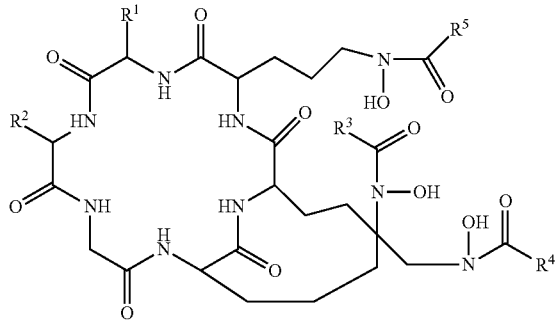

wherein $R^1$ represents a hydrogen atom or a hydroxymethyl group; $R^2$ represents a hydrogen atom, a methyl group, or a hydroxymethyl group; $R^3$, $R^4$, and $R^5$ each independently represent a methyl group, an $N^5$-(trans-5-hydroxy-3-methylpento-2-enoyl) group, an $N^5$-(cis-5-hydroxy-3-methylpento-2-enoyl) group, or an $N^5$-(trans-4-carboxy-3-methylpento-2-enoyl) group.

2. The method according to claim 1, wherein $R^1$ and $R^2$ are hydrogen atoms and $R^3$ to $R^5$ are methyl groups.

3. The method according to claim 1, wherein the tumor is a gastrointestinal cancer.

4. The method according to claim 1, wherein the tumor is a colorectal cancer, a pancreatic cancer, a gastric cancer or an esophageal cancer.

5. A method for preventing a tumor in a subject in need thereof, comprising administrating the subject a compound represented by the following formula (1) or a complex thereof with a metal ion in an amount of 10-2000 μg per kg of body weight of the subject,

[Formula 1]

(1)

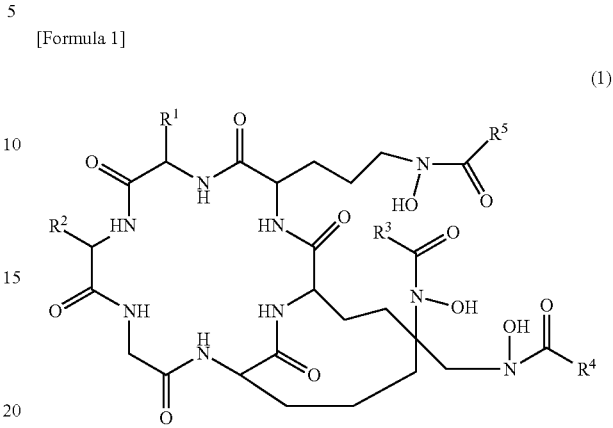

wherein $R^1$ represents a hydrogen atom or a hydroxymethyl group; $R^2$ represents a hydrogen atom, a methyl group, or a hydroxymethyl group; $R^3$, $R^4$, and $R^5$ each independently represent a methyl group, an $N^5$-(trans-5-hydroxy-3-methylpento-2-enoyl) group, an $N^5$-(cis-5-hydroxy-3-methylpento-2-enoyl) group, or an $N^5$-(trans-4-carboxy-3-methylpento-2-enoyl) group.

6. The method according to claim 5, wherein $R^1$ and $R^2$ are hydrogen atoms and $R^3$ to $R^5$ are methyl groups.

7. The method according to claim 5, wherein the tumor is a gastrointestinal cancer.

8. The method according to claim 5, wherein the tumor is a colorectal cancer, a pancreatic cancer, a gastric cancer or an esophageal cancer.

\* \* \* \* \*